(12) United States Patent
Gemmati

(10) Patent No.: US 10,067,132 B2
(45) Date of Patent: Sep. 4, 2018

(54) METHOD FOR DETERMINING FXIII LEVELS AS A PROGNOSTIC BIOMARKER IN ACUTE MYOCARDIAL INFARCTION

(71) Applicant: Donato Gemmati, Ferrara (IT)

(72) Inventor: Donato Gemmati, Ferrara (IT)

( * ) Notice: Subject to any disclaimer, the term of this patent is extended or adjusted under 35 U.S.C. 154(b) by 0 days.

(21) Appl. No.: 15/228,130

(22) Filed: Aug. 4, 2016

(65) Prior Publication Data

US 2016/0363592 A1 Dec. 15, 2016

Related U.S. Application Data

(62) Division of application No. 14/316,263, filed on Jun. 26, 2014, now abandoned.

(30) Foreign Application Priority Data

Jun. 27, 2013 (IT) .............. TO2013A0532

(51) Int. Cl.
*G01N 33/53* (2006.01)
*A61K 38/36* (2006.01)
*A61P 9/10* (2006.01)
*G01N 33/573* (2006.01)
*G01N 33/86* (2006.01)
*C07K 14/745* (2006.01)
*C07K 16/36* (2006.01)

(52) U.S. Cl.
CPC .......... *G01N 33/573* (2013.01); *A61K 38/36* (2013.01); *A61P 9/10* (2018.01); *G01N 33/53* (2013.01); *G01N 33/86* (2013.01); *C07K 14/745* (2013.01); *C07K 16/36* (2013.01); *G01N 2333/91085* (2013.01); *G01N 2800/324* (2013.01); *G01N 2800/52* (2013.01)

(58) Field of Classification Search
None
See application file for complete search history.

(56) References Cited

U.S. PATENT DOCUMENTS

2007/0167361 A1* 7/2007 Inbal ............... A61K 38/45
514/406
2015/0004625 A1 1/2015 Gemmati

FOREIGN PATENT DOCUMENTS

WO WO 92/15609 9/1992

OTHER PUBLICATIONS

Alkjaersig et al, 1977. Thrombos Haemostas. 38: 863-873.*
Italian Search Report for IT TO 2013A000532 dated Dec. 5, 2013.
M. Nahrendorf et al., "Factor XIII Deficiency Causes Cardiac Rupture, Impairs Wound Healing, and Aggravates Cardiac Remodeling in Mice with Myocardial Infarction", Circulation, American Heart Association, Inc., vol. 113, No. 9, Mar. 7, 2006, pp. 1196-1202.
M. Nahrendorf et al., "Does FXIII Deficiency Impair Wound Healing After Myocardial Infarction?", PLOS ONE, Public Library of Science, vol. 1, No. 1, Dec. 1, 2006, pp. e48-1.
M. Nahrendorf et al., "Transglutaminase Activity in Acute Infarcts Predicts Healing Outcome and Left Ventricular Remodeling; Implications for FXII Therapy and Antithrombin Use in Myocardial Infarction", European Heart Journal, vol. 29, No. 4, Feb. 1, 2008, pp. 445-454.
A. Kappel et al., "Fully Automated Immunoassay for Quantitative Determination of FXIII", Haemostaseologie, Stuttgart, vol. 31, No. 2, May 2, 2011.
Reynolds et al, "Safety, pharmacokinetics, and immunogenicity of single-dose rFXIII administration to healthy volunteers", Journal of Thrombosis and Haemostasis, 2005, 3:922-928.

* cited by examiner

*Primary Examiner* — Zachary C Howard
(74) *Attorney, Agent, or Firm* — Nixon & Vanderhye PC

(57) ABSTRACT

A diagnostic method for determining prognosis of a myocardial infarcted patient, wherein the amounts of FXIII protein are determined on the day of myocardial infarction (t0) and at least on the following three days (t1 to t3), wherein a lowering of FXIII amount on any one of t0 to t3 below a threshold value is indicative of an increased risk of poor prognosis.

15 Claims, 2 Drawing Sheets

METHOD FOR DETERMINING FXIII LEVELS AS A PROGNOSTIC BIOMARKER IN ACUTE MYOCARDIAL INFARCTION

This is a divisional of application Ser. No. 14/316,263, filed Jun. 26, 2014 (published as US 2015-0004625 A1), which claims priority to Italian Patent Application IT TO2013A000532 filed 27 Jun. 2013, the entire contents of each of which is hereby incorporated by reference.

FIELD OF THE INVENTION

The present disclosure concerns a novel prognostic biomarker in acute myocardial infarction.

BACKGROUND ART

After acute myocardial infarction (AMI), the damaged heart tissue starts a complex series of processes aimed to repair, and eventually to replace, the lesion by scar tissue [1].

During this period, the infarcted area is highly active biologically. A rapid turnover of cells and of structural components contributes to create new extracellular matrix (ECM). Preexisting ECM proteins (e.g. collagen) are digested by metalloproteinases (MMPs) and new matrix is laid down. Contextually, new cell migration and differentiation contribute to myocardial recovery after injury [1,2].

Starting from the earliest phases of wound repair, attempted by the extensive changes of tissue architecture, the vulnerable wound is exposed to the mechanical stress of the continuous heart beating cycles. This is, besides, responsible for drastic changes of the intraventricular pressure and volume. During the healing processes, myocardial contraction cannot be avoided, so the lesion cannot ever heal properly, if compared to other tissue lesions in which the mechanical stress is extremely lower and they can also be contained by provisional rigid scaffold/tutors (i.e. skin lesions, bone fractures, etc).

Although all the specific reparative processes are potentially appropriate and well-timed, very often they fail in avoiding adverse remodelling and loss of myocardial performances due to non-optimal scar formation at the injury site or even to scar rupture.

The first step (attempt) in the reparative processes after wound occurs is the formation of a three-dimensional fibrin meshwork aimed to block lesion expansion and furnish a provisional scaffold/platform for endogenous neo-vessels formation, cell recruiting and spreading. The earlier the process starts, the better the healing is due to prompt scar formation. In addition, proper healing steps should not be interrupted or hampered by enzymatic and/or mechanical actions (e.g. fibrin meshwork rupture due to unrestrained proteolytic activity or heart beating), specially in the earliest healing phases.

Normally, a high strength together with an extraordinary extensibility and elasticity of the fibrin net is warranted by the action of a circulating transglutaminase, factor XIII (FXIII), which by means of covalent cross-bonds links fibrin chains and several other ECM components changing drastically their original properties [3]. This fact lets the fibrin-scaffold to work properly by counteracting lesion expansion and furnishing the best setting and timing to have an optimal reparative process. Finally, cell migration/differentiation and neo-vessel formation are FXIII-dependent processes and strongly contribute to myocardial healing and recovery after injury.

FXIII is a pro-enzyme of plasma transglutaminase family, consisting of two enzymatic A subunits (FXIII-A) and two non-catalytic B subunits (FXIII-B) [3]. It plays a critical role in generation of a stable haemostatic plug, wound healing, tissue repair, and angiogenesis. FXIII is present in plasma, platelets, monocytes, and macrophages, all components deeply involved in infarct healing. Its key role on healing is demonstrated by the following:

(1) delayed haemorrhage in congenital FXIII deficient subjects;
(2) delayed wound healing in FXIII-deficient cases by human and animal models;
(3) positive effects by FXIII topical application on wound healing by in vivo and in vitro studies;
(4) antiapoptotic and proangiogenic properties;
(5) effects on cell migration/differentiation into the wound;
(6) modulation of fibrin and new collagen synthesis and deposition in ECM;
(7) strong positive effects in heart transplanted animals.

Extraordinary direct evidences of the essential role of FXIII in acute and chronic infarct scar stability come from an experimental model with genetically reduced FXIII levels in animals. Nahrendorf and coll. In 2006 [4], in mice deficient in (FXIII−/−), or heterozygous for (FXIII−/+) the FXIII-A gene (FXIII levels 5% and 70% respectively), by means of coronary ligation and high-field cardiac MRI, followed myocardial scar formation and the consequent remodelling process of the heart. Authors found that all and FXIII−/− mice died within 5 days after MI due to left ventricular rupture. On the contrary, FXIII−/− mice that received five days of intravenous FXIII replacement therapy had normal survival rates; though, their cardiac MRI demonstrated worse left ventricular remodelling. Again, by using a FXIII-sensitive molecular imaging probe, they found significantly greater FXIII activity in wild-type mice and in reconstituted FXIII−/− mice than in non-reconstituted FXIII−/− mice. Contextually, neutrophil cell migration into the MI scar was diminished in FXIII−/− mice but not in reconstituted FXIII−/− mice, and the physiological MMP-9 increasing, normally observed after MI, was 650% higher [4]. in non-reconstituted FXIII−/− mice. This, together with the observation that collagen-1 level was 53% lower in FXIII−/− mice, demonstrate an imbalance in ECM turnover and provides a possible explanations for the observed cardiac rupture in 100% of the FXIII deficient mice. In confirmation of the latter, mice KO for MMP-9 gene were protected against cardiac rupture and they survived. Thus, prevention of unrestrained MMP-9 upregulation by FXIII efficiently contributes to protection against post-MI cardiac rupture.

After the publication of Nahrendorf [4], several other papers reported data in favour of the extraordinary role of FXIII in the post-MI healing fate. Most of them dealt with poor healing and adverse remodelling as the primary cause of heart failure [5,6]. Other suggested FXIII as "The cement of the heart after myocardial infarction" [7], able to contrast infarct expansion and suggesting FXIII as a useful replacement therapy in patients with ventricular rupture [5].

The direct pro-healing properties of FXIII in post-infarcted heart. (i.e angiogenesis and cell proliferation/differentiation) and those mediated by the FXIII-stabilized matrix into the wound (i.e. modulation of fibrin and new collagen synthesis/deposition) prompted researchers even to propose intra-myocardial injections of polymeric biomaterial components or utilization of fibrin-cell-seeded scaffold in the first phases of MI. This could help in reducing infarct size and facilitating stem cell or growth factors delivery improving in turn better heart healing and higher survival [8,9].

Finally, the recently recognized role of the cellular immune response as essential in myocardial healing, ascribe to neutrophils, and monocytes/macrophages key functions in post-MI healing [10-13]. Briefly, in the first hours after ischemia, neutrophils accumulate in the infarcted myocardium and peak about within 24 hours; thereafter, monocytes/macrophages invade the lesion. Divergent and complementary functions have been associated to different monocyte subsets during the complex healing phases. In the inflammatory phase, neutrophils, and monocytes migrate in the infarcted myocardium to remove dead cells and debris and promote ECM degradation by activated MMPs; subsequently, monocytes/macrophages produce cytokines to repress inflammatory signals and regulate the formation of granulation tissue, essential for the proliferative phase. Now, new blood vessels, fibroblast proliferation, and ECM formation, favourite the maturation phase in which this tissue is substituted by a mature collagen based scar.

FXIII takes part to all of these functions, being at the intersection of coagulation, inflammation as well as wound healing [3]. In fact, recruitment of both macrophages and neutrophils are reduced in the infarcted heart of FXIII−/− KO mice as well as phagocytic activity. FXIII is also contained in these particular inflammatory cells, and it basically furnishes a more robust tri-dimensional meshwork with augmented elastic and extensible properties. This facilitates new vessel formation and cell differentiation avoiding imbalance in ECM turnover and attenuating inflammatory response to injury.

All the data described above are in favour that having appropriate levels of FXIII at the injury site is essential requisite for optimal wound healing particularly in the earliest phases. Accordingly, recent reports strongly suggest the needing to explore new treatment strategies to repair the injured heart, by augmentation of intrinsic wound healing that occurs during the first 1 to 2 weeks after MI. This also because on one hand the existence of efficient acute care (angioplasty, thrombolyses) have reduced drastically acute infarct mortality, and on the other the inadequate options to treat the increased number of infarct survivors has contributed to the growth of post-MI chronic complications in particular heart failure [1].

Accordingly, other studies suggest that a prompt FXIII supplementation could help heart in healing itself, because of the lack/deficiency of this enzyme invariably leads to the worst-prognosis of healing after myocardial injury [5,6,14]. Although intervening at this step is considered a promising, but underexploited, useful time window between acute reperfusion efforts and therapy against anomalous cardiac remodelling/chronic heart failure, one must be cautious and keep in mind that FXIII stabilizes blood clots (thrombus) which presence in coronaries is just responsible for occlusion/infarction [4].

The quality of infarct healing shortly after myocardial injury marks the fate of the patient for years to come. Nowadays, there no exist dedicated laboratory tests to efficiently predict post-MI healing outcome and/or to have prognostic information to help clinicians in earlier applying personalized treatment to avert anomalous ventricular remodelling and heart failure or other major adverse cardiac events (MACE).

OBJECT AND SUMMARY OF THE INVENTION

Object of the represent invention is to provide a novel biomarker for determining prognosis of a patient who suffered a myocardial infarction.

According to the invention, the above object is achieved thanks to the compositions specified in the ensuing claims, which are understood as forming an integral part of the present description.

In an embodiment, the present disclosure provides for a diagnostic kit for evaluating FXIII levels in a myocardial infarcted patient, having FXIII levels prognostic value about recovery of the patient, wherein the kit comprises means for detecting FXTII levels in biological samples of said patient, and at least four sample collecting tubes suitable to collect at least four patient biological samples taken on the day of myocardial infarction (t0) and at least on the following three days (t1 to t3).

A further embodiment of the instant disclosure concerns a diagnostic method for determining prognosis of a myocardial infarcted patient, wherein the levels of FXIII protein are determined on the day of myocardial infarction (t0) and at least on the following three days (t1 to t3), wherein a lowering of FXIII level on any one of t0 to t3 below a threshold value is indicative of a poor prognosis.

The present disclosure provides the evidence that FXIII level monitoring in the very early phases of myocardial infarction helps the clinicians in predicting infarction evolution with particular interest in the possible post-myocardial infarction major adverse, cardiac events establishment and consequently determining therapeutic treatments.

BRIEF DESCRIPTION OF THE ANNEXED DRAWINGS

Further features and advantages of the invention will become apparent from the detailed description which follows and which is given purely by way of non limiting examples with reference to the annexed figures of drawings. These drawings are essentially in the form of diagrams showing exemplary delivery profiles of various active agents that may be achieved using compositions as described herein. Specifically:

FIG. 1: Mean and Median values of FXIII levels at the scheduled time in the whole cohort of MI patients analyzed.

FIG. 2A: Mean and Median values of FXIII levels at the scheduled time in those cases who did not experience MACEs during the follow-up.

FIG. 2B: Mean and Median values of FXIII levels at the scheduled time in those cases who experienced or kind of MACE during the follow-up.

FIG. 3A: Mean and Median values of FXIII levels at the scheduled time of patients having a MACE who did not experience AMI (re-infarction) as first end-point in the follow-up after the first acute MI.

FIG. 3B: Mean and Median values of FXIII levels at the scheduled time of patients who experienced AMI (re-infarction) as first end-point in the follow-up after the first acute MI.

FIG. 4A: Mean and Median values of FXIII levels at the scheduled time in those patients who experienced heart failure (HF).

FIG. 4B: Mean and Median values of FXIII levels at the scheduled time in those patients who deceased during the follow-up, t30 was not reported due to the partial and scanty availability of samples (see results).

FIG. 5: Mean and Median values of FXIII levels at the scheduled time in those patients who experienced unstable angina as main symptom during the follow-up.

FIG. 6: ROC curve of FXIII at day 4th (t4*); the associated informative details are reported in Table 1.

DETAILED DESCRIPTION OF THE INVENTION

In the following description, numerous specific details are given to provide a thorough understanding of embodiments. The embodiments can be practiced without one or more of the specific details, or with other methods, components, materials, etc. In other instances, well-known structures, materials, or operations are not shown or described in detail to avoid obscuring aspects of the embodiments.

Reference throughout this specification to "one embodiment" or "an embodiment" means that a particular feature, structure, or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

The headings provided herein are for convenience only and do not interpret the scope or meaning of the embodiments.

The present disclosure concerns the identification of a novel biomarker useful in determining potential recovery of patients who suffered a myocardial infarct.

In an embodiment, the present description provides for a diagnostic kit for evaluating FXIII amounts in a myocardial infarcted patient, having FXIII amounts prognostic value about recovery of the patient, wherein the kit comprises means for detecting the amount of FXIII protein in at least four, preferably six, biological samples and at least four, preferably six, sample collecting tubes suitable to collect the at least four, preferably six, patient biological samples taken on the day of myocardial infarction (t0) and at least on the following three to five days (t1 to t3 or t1 to t5).

A still further embodiment of the instant disclosure concerns a diagnostic method for determining prognosis of a myocardial infarcted patient, wherein the amounts of FXIII protein are determined on the day of myocardial infarction (t0) and at least on the following three days (t1 to t3), wherein a lowering of FXIII amount on any one of t0 to t3 below a threshold value is indicative of a poor prognosis.

In a further embodiment, the threshold value of FXIII protein amount is evaluated as a percentage of a FXIII protein reference value conventionally fixed as 100% (if not differently reported) of a reference sample (normal control), wherein such a reference sample is obtained by standard reference materials like for example reference calibration lyophilized pooled plasma.

As an example, the threshold value (or cut-off value), below which the patient is at risk of a poor prognosis (i.e. heart failure or death), varies according to the time considered (t0-t5). All the thresholds are expressed as percentage of FXIII protein amount of the normal control (reference). The threshold values for t0 to t5 (determined by the ROC analysis), provided appreciable and significant results, i.e. allowed to correctly determine the prognosis of an infarcted patient. Accordingly, in the example below, patients who developed heart failure or those who died after AMI are joined together because of their behaviours (in FXIII consumption) are very similar. Hence, comparing by the ROC procedure the FXIII levels of this MACE+ subgroup with the FXIII levels of all the MACE− group, the results were statistically significant.

In table 1 the threshold values of FXIII protein amount on any of t0 to t5 are provided.

TABLE 1

| Time | FXIII % Cut-off (ROC) | Sensitivity/ Specificity (%) | P | AUC | CI (95%) |
|---|---|---|---|---|---|
| t0 | 88.0 | 69.23/70.43 | <0.0001 | 0.720 | 0.663-0.769 |
| t1 | 87.7 | 65.45/66.67 | <0.0001 | 0.700 | 0.638-0.754 |
| t2 | 85.8 | 65.31/67.05 | <0.0001 | 0.710 | 0.644-0.768 |
| t3 | 75.6 | 64.44/75.94 | <0.0001 | 0.760 | 0.709-0.800 |
| t4* | 74.9 | 74.29/67.01 | <0.0001 | 0.740 | 0.677-0.787 |
| t5 | 63.0 | 73.33/76.00 | <0.0001 | 0.770 | 0.660-0.855 |

ROC = Receiver Operating Characteristic;
AUC = Area Under Curve;
CI (95%) = Confidence Interal (95%).
The reported thresholds were obtained comparing the FXIII levels of the MACE+ (heart failure and death) with the whole MACE− subgroup.

The content of Table 1 indicates that the prognostic value of FXIII is already informative in the earliest times (t0-t3). Anyhow, the monitoring of FXIII in a quite complete way (t0-t5) is recommended, because it is difficult to exactly predict the degree of FXIII protein consumption for any infarcted patient. As an example, the ROC curve at day 4 (t4; FXIII cut-off=74.9%) is provided in FIG. 6.

Today, FXIII assays are performed to determine the amount and/or activity of this enzyme in blood to understand if the enzyme level may be responsible or not for a determined pathological/clinical condition, generally haemorrhage. The test, if performed in "acute" condition (i.e. haemorrhage), must always be confirmed in a steady-state-condition far from the acute event. The assay is performed as an individual single test, that is sufficient for a definite diagnosis.

Conversely, the instant disclosure provides data about the prognostic value of FXIII levels in post-infarcted patient: monitoring in acute phase the FXIII levels on a time window of four, preferably six, days (i.e. on the day of acute myocardial infarct (t0) and on the following three to five days (t1 to t3 or t0 to t5)) allows to predict the healing potential (the degree to heal) of such a patient, regardless other associated and/or concomitant interfering/confounding factors.

The experimental data herein collected provide evidence that the acute FXIII fall, due to heart injury, virtually happens in quite all myocardial infarction patients but at different extent. This is caused by both coronary thrombus formation and tissue healing/myocardial scar formation. In detail, the present inventor found that a patient undergoing excessive FXIII consuming at the time of myocardial infarct (MI) is more prone to develop severe heart failure or death, whereas less drastic consuming is found in patients relapsing with re-infarction or u-angina.

Having low/not optimal FXIII levels during the critical scar formation phase hampers heart healing giving back not properly tissue repair with chronic future consequences on myocardial performances. In this restricted period of time, the quality of infarct healing determines the fate of the patient for years to come.

Monitoring of FXIII levels during the acute MI enables clinicians to early discover those patients at risk of poor post-MI prognosis giving the possibility to intervene with targeted treatments.

Additionally, FXIII monitoring allows to recognize in advance those patients really in need to receive Possible FXIII infusion therapy (to ameliorate myocardial healing); indiscriminate FXIII infusion is, in fact, responsible of undesirable pro-clotting function before reliable coronary reperfusion after infarction is completely re-established and must be performed only in patients with actual need thereof.

Taken together, these observations indicate FXIII a useful prognostic biomarker with potential prospective in therapeutic handling of a patient after MI.

The present invention describes how different degrees in the fall of FXIII levels allow to predict the risk to experience the major post-MI adverse cardiovascular events.

So monitoring the amount of FXIII drop observed in the acute MI phases allows prognosticating whether such a patient is at risk to develop future accidents.

The need to have an effective prognostic test is mainly due to the fact that starting from the seventies, large part of efforts in the cardiovascular field have been addressed to diagnostic and surgical (intervention) procedures reaching exceptional results. Due to these effective actions, the rate of patients who survived MI drastically improved and they continue to rise.

The present invention concerns a test able to recognize in advance those patients at increased risk to develop additional cardiovascular accidents in order to approach them with a tailor-made therapeutical treatment.

Nowadays, does not exist a prognostic test or a specific treatment to effectively avert the adverse events secondarily to MI; there exists, in fact, a restricted period of time (1-2 weeks from the establishment of MI) during which it is possible to act in order to potentiate the intrinsic healing power of the heart and thus saving patients from death.

For these reasons, the present disclosure concerns the assessment and monitoring of FXIII levels in the routine laboratory-test-profile for acute myocardial infarction (AMI) detection. The classical marker tests for myocardial infarction are merely passive indicators of heart damage, though very precocious and informative diagnostic tools. Conversely, the complex combined test evaluation herein disclosed results in precious prognostic information very useful for the clinicians. Once verified the diminished FXIII levels it could be possible to act by adjunctive (also therapeutic) treatments. Assessment and monitoring of FXIII levels can also be combined with the classical ischemic markers.

Materials and Methods
Patients and Methods 350 acute MI patients (whole group; mean age 68.2±12.95 years; 72.8% men) admitted to the Emergency Department of the University-Hospital of Ferrara were recruited.

Inclusion criteria were: prolonged chest pain occurring at rest accompanied by electrocardiography (ECG) ischemic changes. CK-MB and/or Troponin-I values were greater than the upper reference limit in two separate blood samples.

All noteworthy patient characteristic are reported in Table 2.

TABLE 2

|  | Total (n = 350) | STEMI (n = 252) | NSTEMI (n = 98) | P |
| --- | --- | --- | --- | --- |
| Age (y, SD, range) | 68.2 ± 12.95 (31-80) | 67.1 ± 13.50 (31-80) | 71.05 ± 11.33 (38-80) | <0.05 |

TABLE 2-continued

|  | Total (n = 350) | STEMI (n = 252) | NSTEMI (n = 98) | P |
| --- | --- | --- | --- | --- |
| Male (n, %) | 255 (72.8) | 186 (73.8) | 69 (70.4) | NS |
| PCI (n, %) | 316 (90.3) | 235 (93.25) | 81 (82.6) | <0.05 |

PCI = percutaneous coronary intervention;
STEMI = patients showing ST-segment elevation MI at enrolment;
NSTEMI = patients NOT showing ST-segment elevation MI at enrolment.

Blood Samples

Blood was collected in Trisodium Citrate Coagulation tubes at admission (t0) and every 24 h for additional five days (t1-t5) from the acute MI event. Control samples were drawn at least after 30-days (t30) to have basal FXIII levels far from the acute ischemic events.

To exclude, possible, further in vitro enzyme degradation/activation additional comparative samples were drawn in EDTA plus Aprotinin tubes.

Plasma was obtained by blood centrifugation at 2500 g×10 min at room temperature, and different aliquots were frozen at −80° C.

In order to verify, in actual fact, how different collection tubes could influence the results, additional MI patients (n=45) were recruited and blood was drawn in duplicate by means of both the classical Trisodium Citrate Coagulation tubes and the EDTA plus Aprotinin tubes. The recruitment scheme, was the same as above described (t0-t5, t30) and the plasma obtained was frozen (−80° C.) till the assessment.

FXIII Level Measurements

FXIII antigen levels were assessed by means of a Latex Reagent which is a suspension of uniform size polystyrene latex particles coated with rabbit polyclonal antibodies, highly specific for the A-subunit of FXIII according to the manufacturer's instructions (Instrumentation Laboratory, Milan, Italy). Briefly the method is based on the principle that when a sample (plasma) containing the A-subunit of FXIII is mixed with the Latex reagent included in the kit, the coated latex particles agglutinate. The degree of agglutination is directly proportional to the concentration of FXIII antigen in the sample and is determined by measuring the decrease of transmitted light caused by the aggregates. The test is easy-to-perform, very fast, and routinely practicable.

Follow-up (FU) and Statistics

The primary endpoint was a composite of cardiovascular death, re-infarction, heart failure or unstable angina (u-angina) at one-year. Major adverse cardiac events (MACEs) were retrospectively analyzed as single variable or combined. Continuous data were presented as means±SD, with the significance of differences judged by t-test. Categorical variables were summarized in terms of number and percentages with the significance of differences judged by Chi-Square test. The recognition of the FXIII threshold(s) at any period of time considered (t0-t5) was obtained by means of the Receiver Operating Characteristic (ROC) analysis. Probability was considered significant at a level of P<0.05.

Results

FXIII was tested at the recruitment (t0) and every 24 h for additional five days (t1-t5) from the acute MI event. Control samples were drawn at least after 30-days (t30) to have basal FXIII levels far from the acute ischemic event.

Table 3 shows the results of FXIII monitoring in acute MI patients obtained using standard sample collecting tubes (indicated Trisodium Citrate Coagulation tubes) and sample collecting tubes containing at least one anti-proteolytic agent and at least one anti-coagulating agent (indicated EDTA plus Aprotinin tubes).

Though slightly lower values resulted from the EDTA plus Aprotinin tubes, no significant differences were obtained by comparing the two different vials in which blood was collected. Anyhow, making use of tubes containing at least one anti-proteolytic agent and at least one anti-coagulating agent is recommended in those situations in which a not so rapid assessment of the test can be possible (delay≥4 hours from the time in which blood is taken).

The anti-proteolytic agent can be selected among aprotinin, heparin, antithrombin, hirudin, EDTA (Ethylenediaminetetraacetic acid), EGTA (Ethylene glycol-bis(β-aminoethyl ether) tetraacetic acid), Leupeptin, iodoacetamide, APMSF ((4-Amidino-phenyl)methane-sulfonyl fluoride), 4-(2-Aminoethyl)-benzenesulfonyl-flouride hydrochloride, a2-Macroglobulin.

The use of collecting tubes containing at least one anti-proteolytic agent allows, in fact, to determine the actual FXIII protein amount in the infarcted patient avoiding further consumption of FXIII protein contained in the collecting tube because of the presence of the anti-proteolytic(s) completely blocks any further (in vitro) enzyme activation. This precaution warrants a more reliable FXIII detection, better reflecting that particular in vivo status.

TABLE 3

|  | t0 | t1 | t2 | t3 | t4 | t5 | t30 |
|---|---|---|---|---|---|---|---|
| Trisodium Citrate Coagulation tubes | | | | | | | |
| Mean | 99.48 | 97.68 | 94.72 | 90.72 | 85.24 | 76.51 | 110.15 |
| Median | 98.4 | 95.30 | 94.20 | 88.70 | 83.20 | 74.05 | 108.20 |
| SD | 30.57 | 28.06 | 29.12 | 30.30 | 24.93 | 27.02 | 20.34 |
| min | 40.60 | 39.90 | 32.80 | 29.5 | 20.90 | 20.00 | 60.00 |
| max | 186.40 | 181.10 | 179.80 | 169.10 | 136.20 | 138.25 | 147.90 |
| EDTA plus Aprotinin tubes | | | | | | | |
| Mean | 98.34 | 96.87 | 93.61 | 89.16 | 83.08 | 75.45 | 107.34 |
| Median | 94.40 | 95.15 | 92.30 | 87.90 | 72.65 | 74.00 | 105.90 |
| SD | 31.87 | 32.34 | 34.40 | 31.25 | 28.72 | 29.19 | 27.37 |
| Min | 41.05 | 38.75 | 34.70 | 30.5 | 22.05 | 21.90 | 61.25 |
| Max | 193.90 | 190.90 | 182.50 | 178.20 | 139.60 | 135.25 | 152.70 |
| P | 0.92 | 0.32 | 0.30 | 0.35 | 0.28 | 0.84 | 0.80 |

Figure 1:
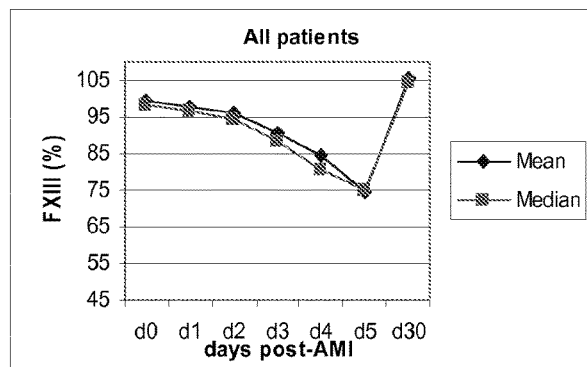
FIG. 1 shows the mean and median levels of FXIII during the assessment period in the whole cohort.
Figure 2A:
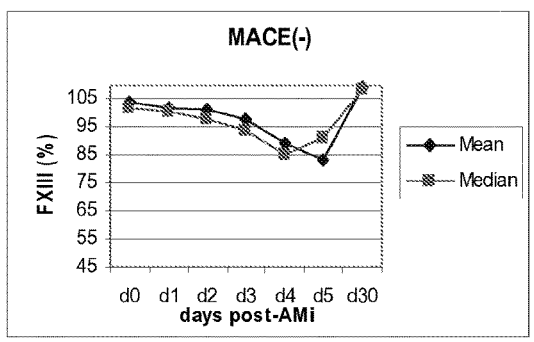
FIGS. 2 to 5 show the FXIII levels in different subgroups of patients during the six days (t0-t5) and at the final check (t30).
Figure 2B:
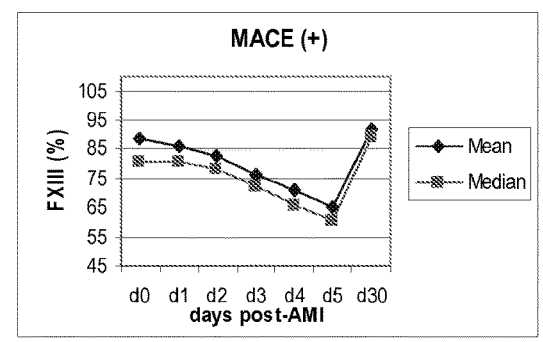

Globally, a significant FXIII level drop was clearly observed at t4-t5 as both mean and median regardless the patients experienced or not major adverse cardiac events (MACE) (FIGS. 2B and 2A, respectively).

Interestingly, the combined endpoint analysis showed that the FXIII fall was significantly stronger considering those patients who experienced major adverse cardiac events (MACE) (MACE+; n=101; 28.8%) when compared with the rest of patients free of major post-MI events (MACE−; n=249; 71.1%).

It's noteworthy the observation that MACE+ patients presented with significantly lower FXIII levels at t0 and at any time considered as both mean and median. The data of FXIII levels in the t0 to t5 time window for MACE− and MACE+ patients are provided in Tables 4 and 5, respectively.

TABLE 4

| MACE− (n = 249) | | | | | | | |
|---|---|---|---|---|---|---|---|
|  | t0 | t1 | t2 | t3 | t4 | t5 | t30 |
| Mean | 103.73 | 102.10 | 101.31 | 98.02 | 89.34 | 83.37 | 109.53 |
| Median | 102.20 | 100.53 | 97.80 | 94.05 | 85.20 | 91.00 | 108.35 |
| SD | 28.77 | 29.17 | 31.55 | 29.74 | 25.58 | 23.53 | 24.95 |
| min | 46.30 | 42.60 | 42.40 | 40.60 | 38.30 | 37.00 | 54.80 |
| max | 236.80 | 201.20 | 198.90 | 193.90 | 149.60 | 136.60 | 172.70 |

TABLE 5

| MACE+ (n = 101) | | | | | | | |
|---|---|---|---|---|---|---|---|
|  | t0 | t1 | t2 | t3 | t4 | t5 | t30 |
| Mean | 88.69 | 86.22 | 82.68 | 76.28 | 71.00 | 65.07 | 91.94 |
| Median | 81.00 | 81.00 | 78.00 | 72.00 | 66.00 | 60.55 | 88.95 |
| SD | 29.41 | 29.87 | 29.71 | 29.10 | 29.01 | 31.12 | 24.28 |
| min | 35 | 32.8 | 31.5 | 30.5 | 20.9 | 18 | 54 |
| max | 167.2 | 160.5 | 158.4 | 151 | 148 | 136.6 | 159 |

Figure 3A:
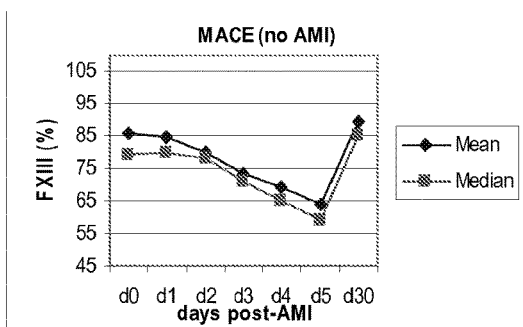
Figure 3B:
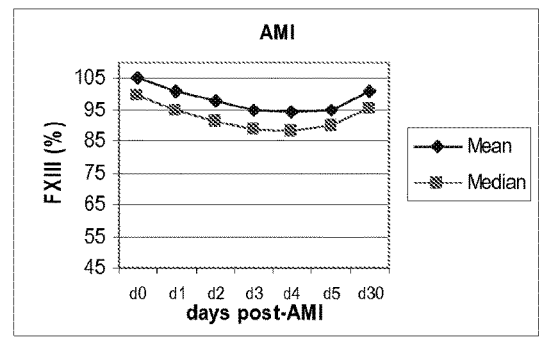

Interestingly, the degree of the FXIII lowering became even stronger in the MACE+ subgroup (FIG. 3A) when those who experienced acute myocardial infarction (AMI) as first end-point in the follow-up were excluded. Indeed, in these latter (AMI), the FXIII drop mean behaviour strongly diverged from the other groups considered, being apparently not affected by a sharp fall of FXIII (FIG. 3B).

Conversely to what happened in the previous described patients (heart failure or dead subgroups), here those who developed AMI, diverge from the other patients being paradoxically less "FXIII-consuming" even than the MACE− group. For this reason we did not compute by ROC analyses this kind of results, but strongly underline their importance suggesting they should be taken in consideration and defer their final interpretation.

To note, these patients (AMI) presented with higher mean FXIII level at t0, and never went below a mean value of 94.0% (t4).

According to the literature on the role of FXIII in recovering of tissue damages, that is low FXIII levels might be responsible for anomalous post-MI heart/wall remodelling causing heart failure or even death (due to inefficient/poor myocardial scar formation at the injury site), the present inventor specifically analyzed how FXIII levels were in those patients who experienced post-MI heart failure (HF) or death.

Figures 4A, 4B:
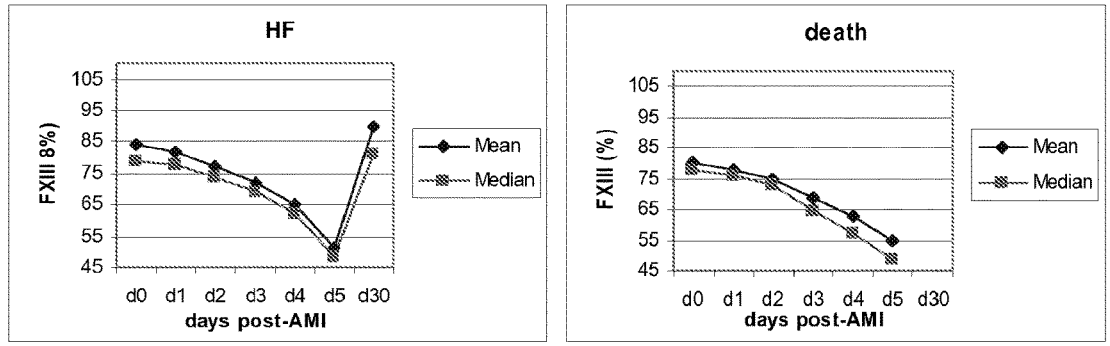

HF patients showed awful FXIII mean reduction and their trend was characterized by a sharper slope. Though they reached very low mean FXIII levels (FIG. 4A), they showed appreciable and normal recovery of FXIII at t30. Conversely, those patients who died due to cardiovascular complications related to the acute experienced MI (FIG. 4B), presented at t0 with slightly lower levels and reached t4-5 with mean and median FXIII values resembling those of the HF subgroup. Unfortunately, t30 was not collected because of large part of these patients died before/or around that time or were definitely not available due to concomitant treatments or complications.

Figure 5:
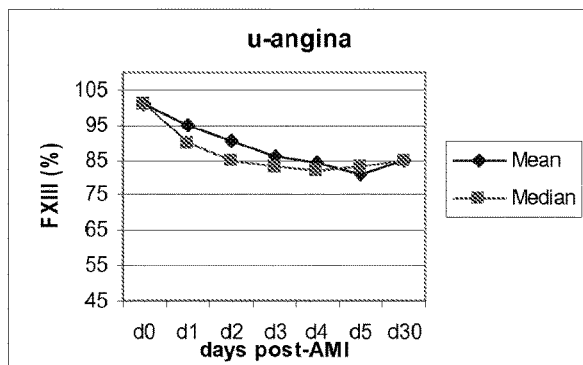
Figure 6:
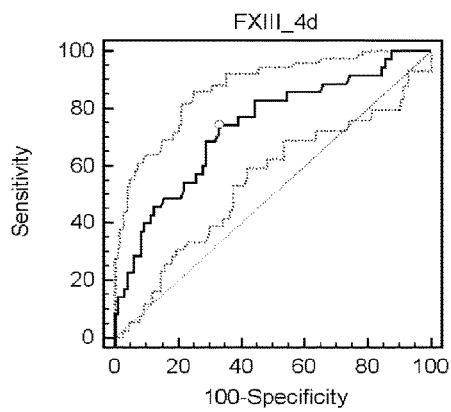

Finally, those patients who experienced u-angina as the prevailing symptom during the follow-up (FIG. 5), though they showed a slow rate in FXIII decreasing, did not show at t30 the classical recover of FXIII levels. This could mean they "continue" to spend/consume FXIII also far from the acute infarction event, possibly due to the chronic relapsing in angina attacks.

Similarly to what we did in the previous less "FXIII-consuming" AMI patients, also data from anginous cases were not computed by ROC analyses. We strongly underline as well, their importance suggesting they should be taken into consideration and defer their final interpretation.

Summarizing, the test/procedure presented here gives very informative results as a prognostic indicator of those MACEs related to excessive FXIII consumption (HF or death). Conversely, though noteworthy, the "low" FXIII consumption observed in anginous and AMI patients deserve future and definite investigations, ascribing anyhow to them a strong potential clinical relevance.

REFERENCES

1. Nahrendorf M, et al. Monocytes: protagonists of infarct inflammation and repair after myocardial infarction. Circulation. 2010; 121:2437-45.
2. Nahrendorf M. Imaging of infarct healing predicts left ventricular remodeling and evolution of heart failure: focus on protease activity. Circ Cardiovasc Imaging. 2011; 4:351-3. doi: 10.1161/CIRCIMAGING.111.966671.
3. Ichinose A. Factor XIII is a key molecule at the intersection of coagulation and fibrinolysis as well as inflammation and infection control. Int J Hematol. 2012; 95:362-70. doi: 10.1007/s12185-012-1064-3.
4. Nahrendorf M, et al. Factor XIII deficiency causes cardiac rupture, impairs wound healing, and aggravates cardiac remodeling in mice with myocardial infarction. Circulation. 2006; 113:1196-202.
5. Nahrendorf M, et al. Does FXIII deficiency impair wound healing after myocardial infarction? PLoS One. 2006, 20;1:e48,
6. Nahrendorf M, et al. Transglutaminase activity in acute infarcts predicts healing outcome and left ventricular remodelling: implications for FXIII therapy and anti-thrombin use in myocardial infarction. Eur Heart. C. 2008; 29:445-54.
7. Vanhoutte D, Heymans S. Factor XIII: the cement of the heart after myocardial infarction? Eur Heart. C. 2008 February; 29(4):427-8. doi: 10.1093/eurheartj/ehm610.
8. Mukherjee et. al. Targeted myocardial microinjections of a biocomposite material reduces infarct expansion in pigs. Ann Thorac Surg. 2008 October; 36(4):1268-76. doi: 10.1016/j.athoracsur.2008.04.107.
9. Della Rocca D G, et al. A degradable, bioactive, gelatinized alginate hydrogel to improve stem cell/growth factor delivery and facilitate healing after myocardial infarction. Med Hypotheses. 2012;79:673-7. doi: 10.1016/j.mehy.2012.03.006.
10. Nahrendorf M, et al. The healing myocardium sequentially mobilizes two monocyte subsets with divergent and complementary functions. J Exp Med. 2007; 204:3037-47.
11. Panizzi P, et al. Impaired infarct healing in atherosclerotic mice with Ly-6C(hi) monocytosis. J Am Coll Cardiol. 2010; 55:1629-33. doi: 10.1016/j.lacc.2009.08.089.
12. Swirski F K, et ai. Leukocyte behavior in atherosclerosis, myocardial infarction, and heart failure. Science. 2013; 339(6116):161-6. doi:10.1126/scdence.1230719.
13. van der Laan A M, et al. Healing and adverse remodelling after acute myocardial infarction: role of the cellular immune response. Heart. 2012; 98:1384-90. doi: 10.1136/heartjn1-2012-301623.
14. Jaffer P A, et al. Molecular imaging of myocardial infarction. J Mol Cell Cardiol. 2006; 41:921-33.

I claim:

1. A method for predicting prognosis of and treating a myocardial infarcted patient, the method comprising:
   providing at least four biological samples of the infarcted patient, the at least four samples being collected on the day of myocardial infarction (t0) and at least on the following three days (t1 to t3);
   determining the amounts of Factor XIII (FXIII) protein in each biological sample; and
   administering FXIII to said patient if the patient has a lowering of FXIII protein amount in any one of t0 to t3 biological samples below a threshold value which is indicative of a poor prognosis in the absence of said administering or any other intervention/treatment.

2. The method according to claim 1, wherein the method further comprises:
   providing at least two further biological samples of the infarcted patient, the at least two further samples being collected on at least the fourth and fifth day following myocardial infarction (t4 to t5);
   determining the amounts of FXIII protein in t4 and t5 biological sample; and
   administering FXIII to said patient if the patient has a lowering of FXIII protein amount in any one of t4 and t5 biological samples below a threshold value which is indicative of a poor prognosis in the absence of said administering.

3. The method according to claim 1, wherein the threshold value of FXIII protein amount is evaluated as a percentage of the FXIII amount of a positive control.

4. The method according to claim 2, wherein the threshold value of FXIII protein amount for each t0 to t5 biological sample is expressed as percentage of FXIII protein amount of a normal control, such amount being fixed to 100%, wherein the threshold values are:

| sample | Threshold (FXIII %) |
|---|---|
| t0 | 88.0 |
| t1 | 87.7 |
| t2 | 85.8 |
| t3 | 75.6 |
| t4 | 74.9 |
| t5 | 63.0. |

5. The method according to claim 1, wherein the patient biological samples are collected in sample collecting tubes containing at least one anti-proteolytic agent and an anti-coagulating agent.

6. The method according to claim 1, wherein the patient biological samples are whole blood, plasma or serum samples.

7. The method of claim 1 wherein determining the amounts of Factor XIII (FXIII) protein is performed by measuring Factor XIII (FXIII) antigen.

8. A method of treating a myocardial infarcted patient having a poor prognosis in the absence of treatment, the poor prognosis being identifiable by a lower than threshold value of Factor XIII (FXIII) protein amount in at least one of four biological samples from said patient, said four biological samples having been collected daily on the day of myocardial infarction (t0) and the following three days (t1 to t3), said method comprising administering FXIII to said myocardial infarcted patient having a poor prognosis.

9. The method of claim 8 wherein said patient has a lower than threshold value of FXIII protein amount in at least one of six biological samples, said six biological samples having been collected daily on the day of infarction (t0) and the following five days (t1 to t5).

10. The method according to claim 8, wherein the threshold value of FXIII protein amount is a percentage of the FXIII protein amount of a positive control.

11. The method according to claim 9, wherein the threshold value of FXIII protein amount for each t0 to t5 biological sample is expressed as percentage of FXIII protein amount of a normal control, such amount being fixed to 100%, wherein the threshold values are:

| sample | Threshold (FXIII %) |
|---|---|
| t0 | 88.0 |
| t1 | 87.7 |
| t2 | 85.8 |
| t3 | 75.6 |
| t4 | 74.9 |
| t5 | 63.0. |

12. The method according to claim 8, wherein the biological samples were collected in sample collecting tubes containing at least one anti-proteolytic agent and an anti-coagulating agent.

13. The method according to claim 9, wherein the biological samples were collected in sample collecting tubes containing at least one anti-proteolytic agent and an anti-coagulating agent.

14. The method according to claim 8, wherein the biological samples are one of whole blood, plasma or serum.

15. The method according to claim 9, wherein the biological samples are one of whole blood, plasma or serum.

* * * * *